(12) United States Patent
Somerville et al.

(10) Patent No.: US 11,931,209 B2
(45) Date of Patent: *Mar. 19, 2024

(54) ULTRASOUND SCANNER AND METHOD OF OPERATION

(71) Applicant: IMV Imaging (UK) Ltd., Bellshill (GB)

(72) Inventors: Adam Somerville, Bellshill (GB); John Fothergill, Bellshill (GB)

(73) Assignee: IMV IMAGING (UK) LTD, Bellshill (GB)

(*) Notice: Subject to any disclaimer, the term of this patent is extended or adjusted under 35 U.S.C. 154(b) by 505 days.

This patent is subject to a terminal disclaimer.

(21) Appl. No.: 17/159,509

(22) Filed: Jan. 27, 2021

(65) Prior Publication Data

US 2021/0145414 A1 May 20, 2021

Related U.S. Application Data

(63) Continuation of application No. 15/907,974, filed on Feb. 28, 2018, now Pat. No. 10,939,896.

(30) Foreign Application Priority Data

Feb. 28, 2017 (GB) ...................... 1703253

(51) Int. Cl.
*A61B 8/00* (2006.01)
*A61B 8/08* (2006.01)
*G06F 1/3203* (2019.01)
*G06F 1/3234* (2019.01)

(52) U.S. Cl.
CPC .............. *A61B 8/56* (2013.01); *A61B 8/4427* (2013.01); *A61B 8/4477* (2013.01); *A61B 8/488* (2013.01); *A61B 8/5207* (2013.01); *A61B 8/546* (2013.01); *G06F 1/3203* (2013.01); *G06F 1/325* (2013.01); *A61B 8/429* (2013.01); *A61B 8/461* (2013.01); *A61B 2560/0209* (2013.01)

(58) Field of Classification Search
CPC ....... A61B 8/56; A61B 8/4427; A61B 8/4477; A61B 8/488; A61B 8/5207; A61B 8/546; A61B 8/429; A61B 8/461; A61B 2560/0209; A61B 8/54; A61B 8/58; G06F 1/3203; G06F 1/325; G01S 7/52017; G01S 7/52096; G01S 15/8906
See application file for complete search history.

(56) References Cited

U.S. PATENT DOCUMENTS

| | | | |
|---|---|---|---|
| 5,873,830 A | 2/1999 | Hossack et al. | |
| 9,427,601 B2* | 8/2016 | Barthe | .................. A61B 8/461 |
| 2012/0053465 A1 | 3/2012 | Kudoh | |
| 2012/0209117 A1* | 8/2012 | Mozes | ................. A61B 8/4245 |
| | | | 600/459 |

(Continued)

*Primary Examiner* — Sanjay Cattungal
(74) *Attorney, Agent, or Firm* — FOX ROTHSCHILD LLP

(57) ABSTRACT

Battery-powered ultrasound scanner for veterinary applications, and operating method. Ultrasound measurements are processed to determine if an ultrasound probe is not being moved and, if it is not being moved, the average rate at which ultrasound pulses is generated, thereby reducing power consumption. The average rate at which ultrasound pulses are generated is reduced step-wise if non-movement persist but increase rapidly when movement recommences.

13 Claims, 5 Drawing Sheets

(56) References Cited

U.S. PATENT DOCUMENTS

| | | | |
|---|---|---|---|
| 2013/0053697 A1* | 2/2013 | Holl | A61B 8/4472 600/459 |
| 2014/0180110 A1* | 6/2014 | Schmedling | A61B 8/4472 600/447 |
| 2016/0331353 A1 | 11/2016 | Ralston et al. | |
| 2017/0105701 A1* | 4/2017 | Pelissier | A61B 8/565 |
| 2018/0242956 A1* | 8/2018 | Somerville | A61B 8/488 |

* cited by examiner

ULTRASOUND SCANNER AND METHOD OF OPERATION

CROSS-REFERENCE TO RELATED APPLICATION

The present application is a Continuation Application of U.S. Nonprovisional patent application Ser. No. 15/907,974, filed Feb. 28, 2018, which claims priority to GB Application No. 1703253.3, filed Feb. 28, 2017, the disclosures of which are incorporated herein by reference in their entirety.

FIELD OF THE INVENTION

The invention relates to the field of ultrasound scanners for medical, particularly veterinary, ultrasound imaging applications.

BACKGROUND TO THE INVENTION

Portable battery-powered veterinary ultrasound scanners are often used in challenging environments, for example outdoors, or in farm buildings, over extended periods of time. Power consumption can be significant and battery lifetime is important. The present invention aims to address the problem of reducing power consumption in a portable battery-powered ultrasound scanner. Reducing power consumption can enable a smaller product size, particularly in a rugged product design with limited cooling (e.g. without a fan).

SUMMARY OF THE INVENTION

According to a first aspect of the invention there is a provided an (e.g. veterinary) ultrasound scanner, the ultrasound scanner comprising:
  an ultrasound probe which comprises one or more ultrasound sources and receivers,
  at least one battery,
  transmit circuitry configured to apply electrical signals to the ultrasound sources to generate ultrasound pulses and transmit them into a scan region,
  receive circuitry configured to measure ultrasound echoes received at the ultrasound receivers from the scan region,
  a beam processor configured to process the measured ultrasound echoes and output ultrasound measurement data, the ultrasound measurement data comprising measurements of ultrasound echoes from each of a series of scan positions in the scan region,
  a controller configured to regulate the transmission of ultrasound pulses into the scan region by the ultrasound source and to process the ultrasound measurement data, or data derived therefrom, to determine an amount of movement of the ultrasound probe, and to reduce the average rate at which ultrasound pulses are generated responsive to the determined amount of movement of the ultrasound probe meeting at least one inactivity criterion.

The invention extends in a second aspect to a method of operating an (e.g. veterinary) ultrasound scanner, the ultrasound scanner comprising an ultrasound probe which comprises one or more ultrasound sources and receivers, (the ultrasound scanner typically also comprising at least one battery), the method comprising:
  the one or more ultrasound sources and receivers generating ultrasound pulses and receiving ultrasound echoes from a scan region,
  processing measurements of the received ultrasound echoes to thereby calculate ultrasound measurement data, the ultrasound measurement data comprising measurements of ultrasound echoes from each of a series of scan positions in the scan region,
  processing the ultrasound measurement data, or data derived therefrom, to determine an amount of movement of the ultrasound probe,
  if the amount of movement of the ultrasound probe thereby detected meets at least one inactivity criterion, reducing the average rate at which ultrasound pulses are generated.

Thus, when it is determined from the ultrasound measurement data, or data derived therefrom, that the at least one inactivity criterion is met, the average rate at which ultrasound pulses are generated is reduced. This reduces power consumption by the transmit circuitry (and in some embodiments by the receive circuitry, beam processor and/or controller).

This contrasts with detecting that an ultrasound probe is no longer in physical contact with a subject by, for example, detecting the absence of ultrasound echoes and so enables power consumption to be reduced if an ultrasound probe is not being moved, even if it does remain in physical contact with a subject. It may be that the ultrasound scanner is further configured to detect an absence of ultrasound echoes in response to ultrasound pulses and to enter a standby mode responsive thereto. The standby mode is a distinct mode. Typically, in at least some circumstances (e.g. mode) in which the average rate at which ultrasound pulses are generated, the average rate at which ultrasound pulses are generated remains at least 10 times (and typically at least 100 times) higher than the average rate at which ultrasound pulses are generated in the standby mode.

The ultrasound measurement data typically comprises data (samples) specifying the measured strength of ultrasound echoes received by one or more ultrasound receivers from the corresponding position within the scan region. By the strength of ultrasound echoes we refer to a parameter relating to the intensity, amplitude or brightness of the ultrasound echoes, in absolute terms or relative to the incident ultrasound pulses.

The one or more ultrasound sources and receivers may comprise an array of ultrasound sources and receivers. However, it is possible that one or more ultrasound sources and receivers is mounted on a support and is swept repetitively along a path in use. In this case a single ultrasound source and a single ultrasound receiver (e.g. a single ultrasound transceiver) may be sufficient.

By scan positions we refer to positions relative to the one or more ultrasound sources and receivers (or the path along which the one or more ultrasound sources and receivers are repetitively moved in use, as appropriate) and thereby relative to the ultrasound probe. The amount of movement of the ultrasound probe may be determined by analysing changes in the ultrasound measurement data, or data derived therefrom, between repeated measurements of the same scan positions, for example:
  by calculating a measure of changes in the strength of ultrasound echoes between measurements (e.g. consecutive measurements) of ultrasound echoes from one or more corresponding positions (typically scan positions);

by processing the ultrasound measurement data, or data derived therefrom, to detect one or more features within the scan region (e.g. boundaries, internal cavities, or points of unusually strong or weak echoes) and processing subsequently obtained ultrasound measurement data, or data derived therefrom, (e.g. measurement data relating to a subsequent ultrasound frame) to determine whether and/or by how much, the one or more features have moved (relative to the ultrasound probe);

by calculating a property of the strength of ultrasound echoes at a plurality of positions (typically scan positions) from the ultrasound measurement data, or data derived therefrom, for example, calculating an average value (e.g. arithmetic mean, median, mode, geometric mean), variance, standard deviation or range of the strength of ultrasound echoes at a plurality of positions (typically scan positions), and calculating a measure of change in that value between measurements (e.g. consecutive measurements) of the corresponding positions (typically scan positions).

Thus the at least one inactivity criteria may comprise that a measure of changes in the strength of ultrasound echoes between measurements (e.g. consecutive measurements) of ultrasound echoes from one or more corresponding positions (typically scan positions) is below a threshold, optionally for at least a predetermined period of time. The at least one inactivity criteria may comprise that the position of one or more features within the scan region determined from the ultrasound measurement data or data derived therefrom, relative to the ultrasound probe (e.g. relative to the array of ultrasound sources and detectors, or the path along which the one or more ultrasound sources and receivers are repetitively moved in use, as appropriate), has moved by less than a threshold amount, optionally over at least a predetermined period of time. The at least one inactivity criteria may comprise that a measure of a change in a property of the strength of ultrasound echoes at a plurality of positions in the ultrasound measurement data, or data derived therefrom, (typically scan positions in the ultrasound measurement data) is less than a predetermined threshold, optionally for at least a predetermined period of time. Said predetermined period of time may, for example, be in the range of 1 to 30 seconds, typically 2.5 to 20 seconds.

It may be that the average rate of generation of ultrasound pulses is reduced in response to detection that a measured temperature within the ultrasound scanner exceeds a first threshold, typically until the measured temperature decreases to below a second threshold (which is the same or a lower temperature than the first threshold). The ultrasound scanner may comprise a temperature sensor.

The ultrasound measurement data is typically divided into ultrasound frames, each ultrasound frame comprising measurements of ultrasound echoes at scan positions distributed across the scan region such that a plurality of ultrasound frames represents a plurality of measurement of ultrasound echoes across the scan region at different (typically consecutive) time, and so can be used to generate consecutive ultrasound images of the scan region.

The scan region is typically scanned as a series of scan lines, extending from the array of ultrasound transmitters and receivers (or the path along which the one or more ultrasound sources and receivers are repetitively moved in use, as appropriate) at different angles. The plurality of scan positions in the scan region typically comprises a plurality of scan positions spaced apart (usually regularly) along each of a plurality of scan lines which extend through the scan region at different angles relative to the array of ultrasound transmitters and receivers (or the path along which the one or more ultrasound sources and receivers are repetitively moved in use, as appropriate). Ultrasound pulses may be focussed along individual scan lines in turn and thereby pass through scan positions along a scan line in turn. Thus the ultrasound measurement data is typically divided into ultrasound line data portions which specify the measured strength (e.g. intensity of amplitude) of ultrasound echoes received by one or more ultrasound receivers from a series of spaced apart position along a line (typically a straight line extending from the ultrasound probe into the scan region).

Typically, the ultrasound measurement data is divided into ultrasound frame data portions (relating to separate ultrasound frames), each of which represents measurements of ultrasound echoes across the scan region, suitable for forming an image frame. In this case, each ultrasound frame data portion typically comprises a plurality of ultrasound line data portions extending through the scan region, e.g. at different angles relative to the ultrasound probe (e.g. relative to the array of ultrasound sources and receivers or the path along which the one or more ultrasound sources and receivers are repetitively moved in use, as appropriate). It is not however necessary for each ultrasound frame data portion to have ultrasound line data portions relating to the same angles relative to the ultrasound receivers and transmitters, for example, ultrasound line data portions relating to different scan lines (angles relative to the array of ultrasound sources and receivers (or the path along which the one or more ultrasound sources and receivers are repetitively moved in use, as appropriate)) may be included in alternate ultrasound frame data portions.

There may be a main operating mode (e.g. a default mode or a mode determined wholly or in part by user settings) in which there is a predetermined average rate at which ultrasound pulses are generated. When the average rate at which ultrasound pulses are generated is reduced, that is typically relative to that main operating mode.

The average rate at which ultrasound pulses are generated may be reduced (e.g. relative to a main operating mode) by one or more of:
  reducing the number of scan lines (e.g. per ultrasound frame);
  increasing the period between ultrasound frames;
  periodically stopping generating ultrasound pulses for a period of time and then restarting It is better to reduce the number of scan lines, or increase the period between ultrasound frames, which may cause a degradation of image quality, than to lose continuity of imaging.

It may be that the average rate at which ultrasound pulses are generated is reduced progressively, for example stepwise, responsive to the determined amount of movement of the ultrasound probe meeting at least one inactivity criterion. The period of time taken to progressively reduce the average rate at which ultrasound pulses are generated may for example be in the range of 1 to 30 seconds, for example 2 to 10 seconds.

It may be that the average rate at which ultrasound pulses are generated is reduced, responsive to the determined amount of movement of the ultrasound probe meeting at least one inactivity criterion, through a plurality of different modes which differ in the average rate at which ultrasound pulses are generated, in a predetermined order. The modes may for example differ in terms of one or more of: the number of scan lines per ultrasound frame and/or the period between ultrasound frames.

It is the average rate which is important. It may for example be that in some modes, when ultrasound pulses are generated they are generated in groups and have the same period between pulses within each group, but that that there are periodic (increased) gaps between groups of ultrasound pulses, thereby reducing the average rate of ultrasound pulses generation.

It may be that in the main operating mode, ultrasound measurement data, or data derived therefrom, relating to a first number of scan positions is processed to determine whether the at least one inactivity criterion is met but that in at least one mode with a reduced average rate of generation of ultrasound pulses, a second, lower number of scan positions is processed to determine whether the at least one inactivity criterion, or at least one activity criterion, is met. Thus, fewer ultrasound pulses required to be generated in the reduced power configurations (modes) than would otherwise be the case in order to determine when the average rate of ultrasound pulse generation should increase again.

It may be that, in addition to reducing the average rate of generation of ultrasound pulses (e.g. in one or more reduced power modes) the intensity of ultrasound pulses is reduced.

It may be that, after reducing the average rate at which ultrasound pulses are generated, the controller is configured to (after reducing the average rate at which ultrasound pulses are generated) increase the average rate at which ultrasound pulses are generated again (for example entering the main operating mode) responsive to the determined amount of movement of the ultrasound probe meeting at least one activity criterion (for example, that an inactivity criterion is no longer met).

Thus, the method may comprise continuing to process the ultrasound measurement data to determine an amount of movement of the ultrasound probe, and if the amount of movement of the ultrasound probe thereby detected meets at least one activity criterion, the average rate at which ultrasound pulses are generated is increased.

The average rate at which ultrasound pulses are generated may be increased to the original rate (before the average rate was reduced), e.g. to the average rate of ultrasound pulses generation in the main operating mode (for example, by switching to the main operating mode). It may be that the increase in the average rate at which ultrasound pulses are generated can take place during the scanning of an ultrasound frame (and not only between the scanning of whole ultrasound frames). It may be that the increase in the average rate at which ultrasound pulses are generated takes place in less than 1 second, for example less than 0.5 or less than 0.25 seconds, for example.

It may be that, when the average rate at which ultrasound pulses are generated is reduced, the average rate at which ultrasound pulses are generated is reduced progressively (for example step-wise, such as through the said one or more modes), for example over more than 5 seconds, or more than 10 seconds, but when the average rate at which ultrasound pulses is generated is increased, it is increased more quickly, for example, it may be increased back to the original rate within 1 second. The average rate at which ultrasound pulses are generated may be increased again (for example back to the average rate of main operating mode) without waiting to complete an ultrasound frame.

It may be that in at least some circumstances (e.g. in at least one said mode in which the average rate at which ultrasound pulses are generated has been reduced) the images displayed by the ultrasound apparatus freeze and/or the ultrasound measurement data is frozen (e.g. the same ultrasound frame data is repetitively transmitted). This enables an image to continue to be displayed while the average rate of ultrasound pulse generation (e.g. the number of scan lines in each ultrasound frame, more generally the number of scan positions per ultrasound frame) drops below a level suitable for displaying a high quality image, but enables movement to be detected (at which point the average rate of ultrasound pulses generation increases and an image of sufficient quality can be generated again).

It may be that the receive circuitry is sensitive to the frequency of ultrasound in received ultrasound echoes. It may be that the ultrasound measurement data comprises received ultrasound frequency data, or movement (e.g. velocity) data derived therefrom. It may be that the said ultrasound frequency data, or movement data derived therefrom, is processed to determine an amount of movement of the ultrasound probe. A frequency shift (Doppler shift) caused by movement of the probe may be detected.

Nevertheless, it may be that the ultrasound measurement data does not include received ultrasound frequency data, or data derived therefrom such as or Doppler shift (D-mode ultrasound) measurements. Typically, it is a parameter relating to the intensity of ultrasound echoes which is processed to determine whether the one or more inactivity criteria are met. Thus, movement can be detected without the additional complexity and cost of Doppler mode ultrasound detection.

Typically the ultrasound measurement data (e.g. ultrasound data that is processed) is not ultrasound image data, that is to say it has not been processed to form a two dimensional image, for example it has typically not been subject to scan conversion. By an ultrasound image we refer to a visual representation, in at least two dimensions, of the scan region as indicated by the ultrasound echoes which are received by the ultrasound probe, in response to ultrasound signals being generated by the ultrasound probe. Ultrasound image data is derived from ultrasound measurement data (typically by a process including scan conversion). By processing measurement data, prior to image generation, power consumption can be further reduced. This is because ultrasound image generation is significantly power intensive. It may be that the ultrasound scanner does not generate image data; instead, ultrasound image data may be generated by a separate ultrasound data processor. Thus, it may be that the ultrasound scanner can detect inactivity without a requirement to generate ultrasound image data (which is typically power intensive).

However, in some embodiments data derived from ultrasound measurement data, typically ultrasound image data, is processed to determine the amount of movement of the ultrasound probe. The strength of ultrasound echoes at scan positions (or position interpolated therebetween, e.g. the positions represented by specific pixels), position of features in the images etc. can be analysed to determine movement using motion detection algorithms.

The ultrasound scanner may be a (typically handheld) ultrasound probe (comprising at least one battery). However, the ultrasound scanner may comprise both a first scanner portion (e.g. a scanner body, such as a body worn component) and an ultrasound probe, typically connected to the scanner by a cable. In that case, a temperature sensor, if present, may be in the scanner body.

The ultrasound probe is typically a handheld probe, i.e. configured to be used while held in a single hand by a user. The ultrasound scanner comprises one or more batteries. Typically the ultrasound scanner (and thereby the one or more ultrasound sources and receivers) is powered only by the one or more batteries in operation. Power consumption is an important consideration in ultrasound scanners powered only by one or more batteries within the scanner. It may be that the ultrasound scanner does not comprise a fan. Reducing power consumption can make it more practical to omit a fan, thereby providing a more rugged product.

The ultrasound scanner may be part of ultrasound apparatus which further comprises an ultrasound data processing configured to process ultrasound measurement data to generate ultrasound images of the scan region. The method may comprise further processing the ultrasound measurement data to generate ultrasound images and then outputting the ultrasound images. Generating ultrasound images typically comprises scan conversion. Generating ultrasound images may comprise one or more of: angle compounding, frame smoothing and boundary detection. The image processor may comprise a scan converter. The image processor may comprise one or more of: an angle compounder, a frame smoother and a boundary detection module.

It may be that the ultrasound scanner further comprises a wireless transmitter configured to wirelessly transmit the ultrasound measurement data. The ultrasound scanner may comprise a data compressor configured to process the ultrasound measurement data and a wireless transmitter configured to wirelessly transmit the ultrasound data in compressed form.

The invention extends in a third aspect to ultrasound apparatus comprising the ultrasound scanner of the first aspect and an ultrasound data processor, the ultrasound data processor comprising:
 a wireless receiver configured to receive the ultrasound measurement data transmitted by the wireless transmitter, and
 an image processor configured to process decompressed data output by the data decompressor to form ultrasound images of the scan region, and
 a display interface (and typically also a display, although the display interface may be a video data output interface for use with a separate display) configured to output the ultrasound images formed by the image processor.

In embodiments where the ultrasound measurement data is transmitted in compressed form, the wireless receiver is configured to receive the ultrasound measurement data in compressed form and the ultrasound data processor further comprises a data decompressor configured to decompress the compressed ultrasound measurement data received by the wireless transmitter.

The invention also extends in a fourth aspect to methods according to the second aspect of the invention further comprising transmitting the ultrasound measurement data through a wireless transmitter to a wireless receiver of an ultrasound data processor, and at the ultrasound data processor, processing the ultrasound measurement data to form ultrasound images of the portion of the subject, and outputting the ultrasound images (for example displaying the ultrasound image or outputting video data through an interface). It may be that the method comprises the step carried out at the ultrasound scanner of compressing the ultrasound measurement data, wherein the ultrasound measurement data is transmitting through a wireless transmitter to a wireless receiver of an ultrasound data processor in compressed form and the method comprises the further step carried out by the ultrasound data processor of decompressing the received compressed ultrasound measurement data, and processing the resulting decompressed ultrasound measurement data to form ultrasound images of the portion of the subject.

Accordingly, in some embodiments the ultrasound measurement data is compressed prior to being transmitted through a wireless communications channel comprising the wireless transmitter and the wireless receiver. The compressed ultrasound measurement data is then decompressed and used to generate images. The ultrasound measurement data may be compressed using a variable length code.

The wireless transmitter and receiver are typically radio transmitters and receivers. Typically, they are radio transceivers. It may be that the wireless transmitter and receiver are Wi-Fi transmitters and receivers (e.g. Wi-Fi transceivers). Thus, the compressed data may be transmitted by Wi-Fi. Wi-Fi is a wireless radio transmission protocol specified by the IEEE 802.11 standards. (Wi-Fi is a trade mark of the Wi-Fi Alliance).

The one or more ultrasound sources and receivers may be in the form of an array. The array of ultrasound sources and receivers is typically in the form of a one dimensional array, for example spaced apart along a linear or curved line. The scan region is typically planar (being a cross-section through a region of a subject, in use). The scan region is typically defined by the configuration of the ultrasound sources and receivers, and the transmit circuitry and beam processor.

The ultrasound scanner typically comprises a controller which regulates the rate at which scan positions are scanned. The ultrasound scanner typically comprises at least one processor and memory which stores a program which causes the at least one processor to function as the controller when executed. The transmit circuitry, the receive circuitry, the beam former, (and/or the data compressor where present) and/or the controller may be formed in whole or in part by the processor executing a program stored in the memory. Dedicated transmit circuitry, receiver circuitry and beam former ICs are known in the art.

The ultrasound data processor typically comprises one or more processors and memory storing program code. The ultrasound data processor may be a handheld electronic device, for example a smartphone, tablet or laptop. The image display may be in wired communication with the image processor. However, the image display may be in wireless communication with the image processor, for example the image display may comprise video glasses in wireless communication with the image processor. The image processor (and/or data decompressor where present) may be implemented in whole or in part by a microprocessor of the ultrasound data processor executing program code stored in a memory. The image processor may be implemented in whole or in part by a graphic processor.

One skilled in the art will appreciate that although the one or more ultrasound sources and receivers may comprise ultrasound sources and separate ultrasound receivers, the one or more ultrasound sources and receivers may comprise or consist of ultrasound transducers, for example piezoelectric transducers or capacitive transducers, which function as both ultrasound sources and receivers.

The apparatus and method may be used to scan a region of an animal, typically a non-human animal, for example a farm animal (e.g. a pig, horse, cow or sheep) or a domestic animal (e.g. a cat or a dog).

The invention extends in a fifth aspect to an (e.g. veterinary) ultrasound scanner, the ultrasound scanner comprising:
 an ultrasound probe which comprises one or more ultrasound sources and receivers,
 at least one battery,
 at least one temperature sensor, transmit circuitry configured to apply electrical signals to the ultrasound sources to generate ultrasound pulses and transmit them into a scan region, a controller configured to regulate the transmission of ultrasound pulses into the scan region by the ultrasound source and to reduce the average rate at which ultrasound pulses are generated responsive to the temperature measured by the at least one temperature sensor exceeding a (first) threshold.

The invention extends in a sixth aspect to a method of operating an (e.g. veterinary) ultrasound scanner, the ultrasound scanner comprising:

an ultrasound probe which comprises one or more ultrasound sources and receivers,
at least one battery,
at least one temperature sensor,
transmit circuitry configured to apply electrical signals to the ultrasound sources to generate ultrasound pulses and transmit them into a scan region,
the method comprising measuring a temperature within the ultrasound scanner using the at least one temperature sensor and, responsive to detecting that the measured temperature exceeds a (first) threshold, reducing the average rate at which ultrasound pulses are generated.

The ultrasound scanner typically also comprises:
receive circuitry configured to measure ultrasound echoes received at the ultrasound receivers from the scan region, and
a beam processor configured to process the measured ultrasound echoes and output ultrasound measurement data. Typically the ultrasound measurement data comprises measurements of ultrasound echoes from each of a series of scan positions in the scan region, It may be that the method comprises increasing (and it may be that the controller is configured to increase) the average rate at which ultrasound pulses are generated again responsive to the temperature measured by the at least one temperature sensor dropping below a (second) threshold. The second threshold may be lower than the first threshold.

The average rate at which ultrasound pulses are generated may be reduced as set out above in respect of the first and second aspect of the invention. For example, there may be a main operating mode (e.g. a default mode or a mode determined wholly or in part by user settings) in which there is a predetermined average rate at which ultrasound pulses are generated. When the average rate at which ultrasound pulses are generated is reduced, that is typically relative to that main operating mode.

The average rate at which ultrasound pulses are generated may be reduced (e.g. relative to a main operating mode) by one or more of:
reducing the number of scan lines (e.g. per ultrasound frame);
increasing the period between ultrasound frames;
periodically stopping generating ultrasound pulses for a period of time and then restarting.

It may be that the average rate at which ultrasound pulses are generated is reduced progressively, for example stepwise, responsive to the measured temperature reaching progressively increasing values (e.g. progressively increasing thresholds). It may be that the average rate at which ultrasound pulses are generated is reduced through a plurality of different modes, which differ in the average rate at which ultrasound pulses are generated, in a predetermined order. The modes may for example differ in terms of one or more of: the number of scan lines per ultrasound frame and/or the period between ultrasound frames.

Optional feature disclosed in respect of any aspect of the invention are optional features of each aspect of the invention and in particular further optional features of the fifth and sixth aspects of the invention correspond to the optional features disclosed in respect of the first and second aspects of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
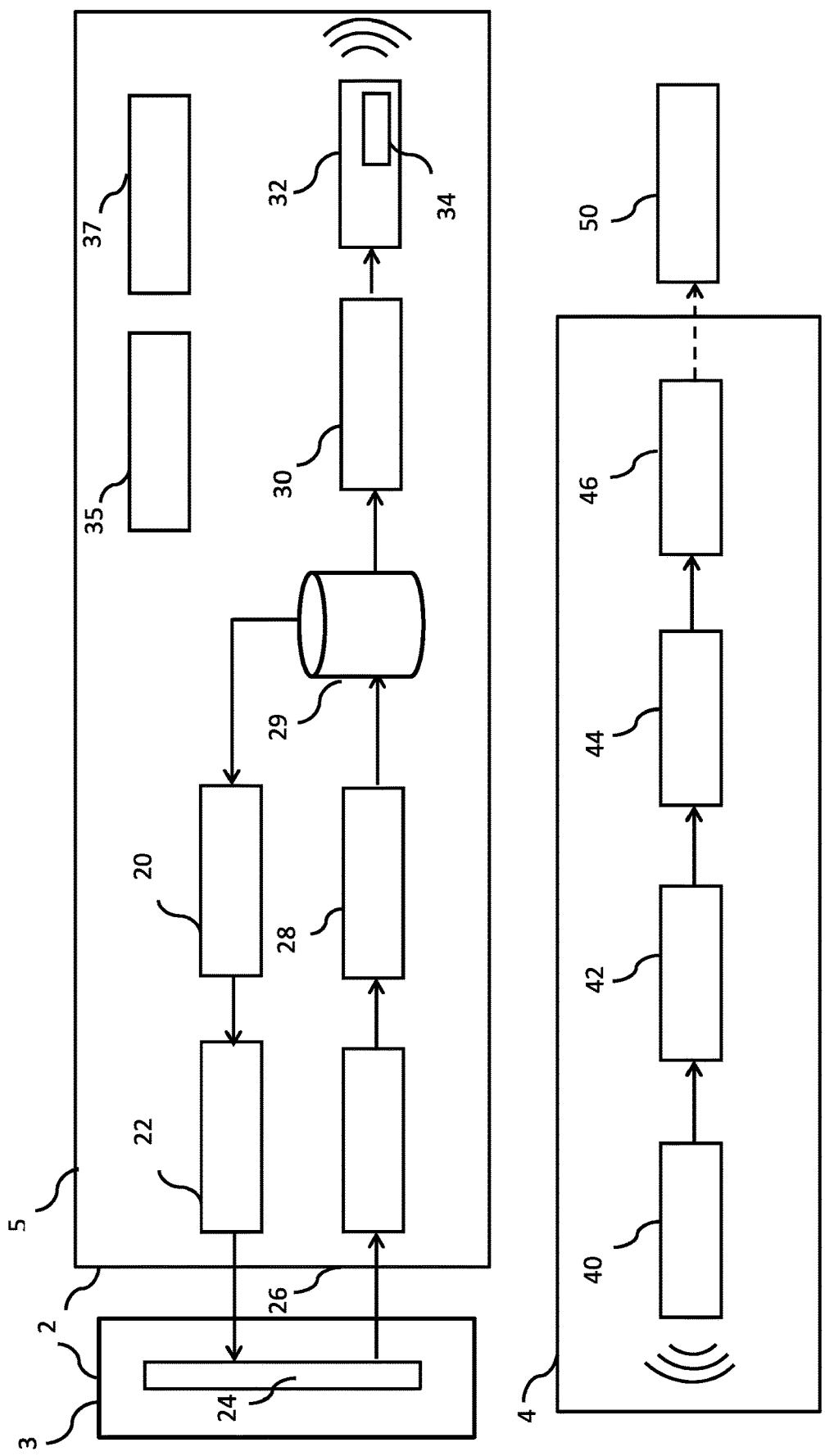
FIG. 1 is a block diagram of ultrasound apparatus including an ultrasound probe.
Figure 2:
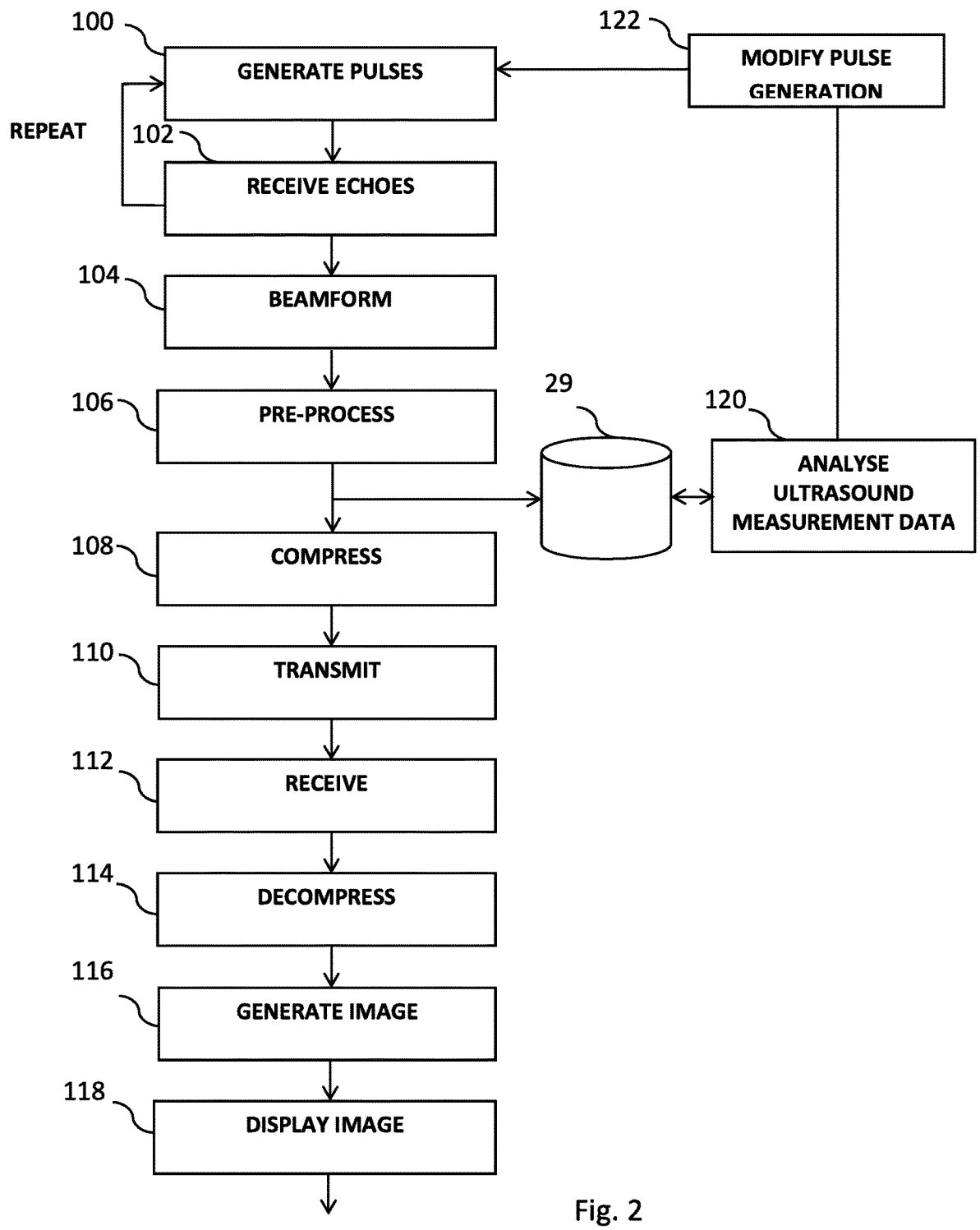
FIG. 2 is a flow diagram of an ultrasound apparatus operating procedure.
Figure 3:
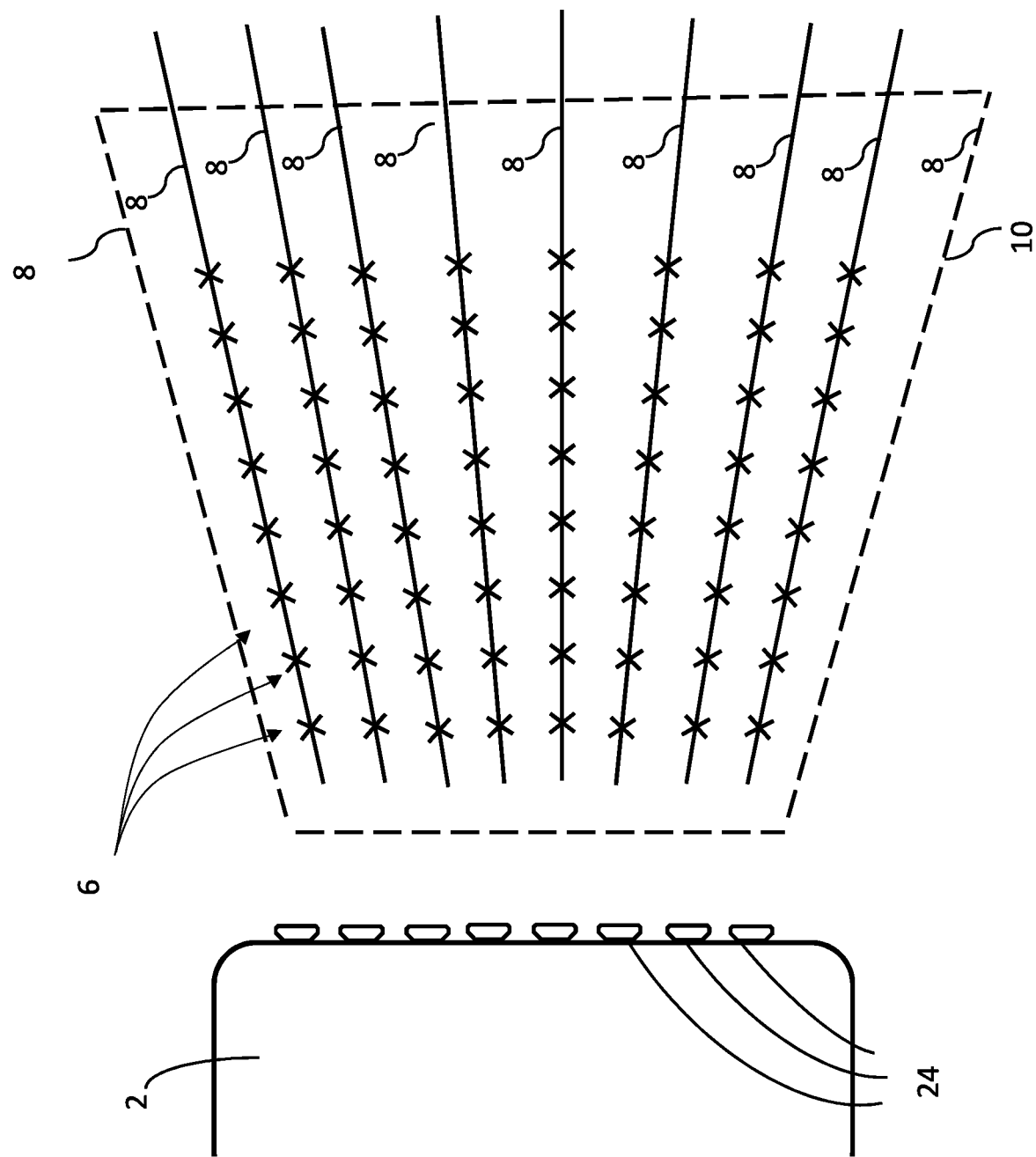
FIG. 3 is a schematic diagram of scan positions located along scan lines within a scan region.
Figure 4:
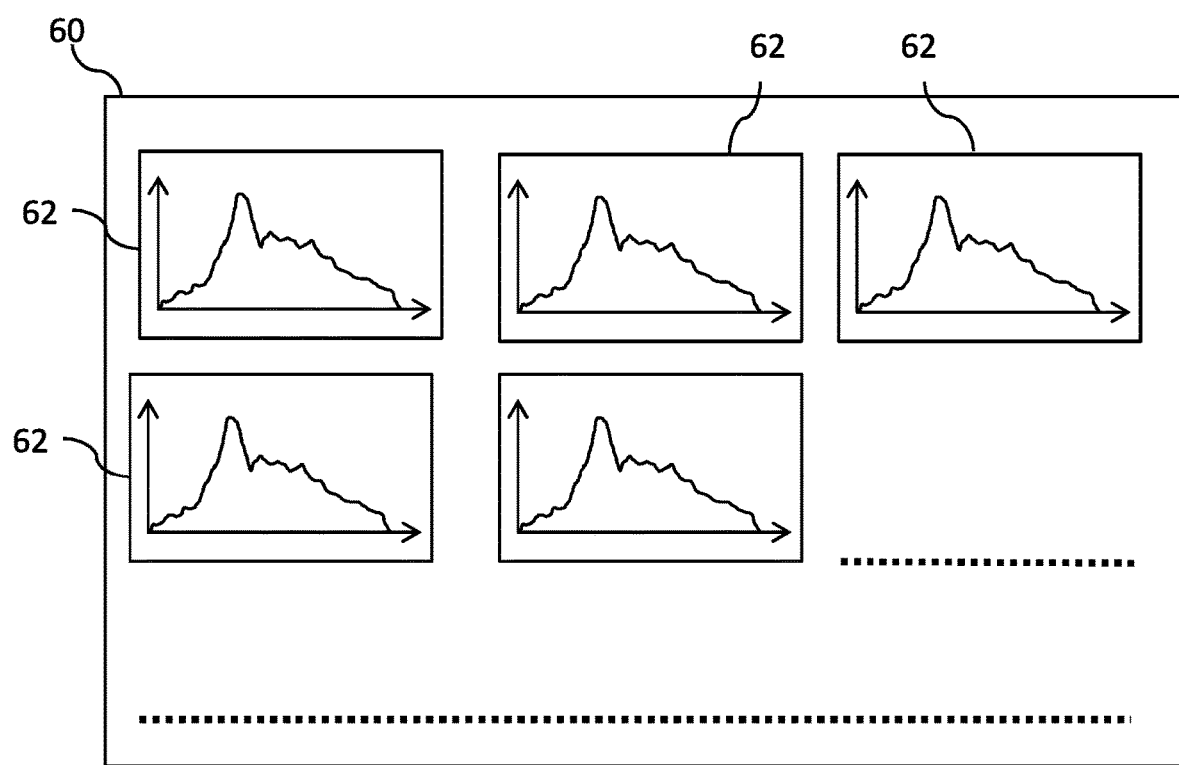
FIG. 4 is a schematic diagram of ultrasound measurement data.

With reference to FIGS. 1 to 3, the invention relates to a hand-held ultrasound scanner 2 which is used with a separate ultrasound data processor 4, together forming ultrasound imaging apparatus. The apparatus is used to generate ultrasound images of a scan region of an animal and to display these images to the user in real time so that the user can rapidly and accurately carry out a scanning task.

In the example of FIG. 1, the ultrasound scanner 2 has a body 5 and a separate handheld ultrasound probe 3, which is the part that is pressed against an animal's flesh in use and which contains the ultrasound transducers 24. The ultrasound probe is connected to the body 5 by a cable. In alternative embodiments, the ultrasound scanner is an integrated ultrasound probe device, with an ultrasound probe region at one end, having the ultrasound transducers, and configured to be handheld.

The ultrasound scanner 2 comprises a processor (e.g. a CPU) executing a stored program, functioning as the controller 20. The controller regulates the scanning procedure, including pulse generation, and data processing and transmission. The controller includes a movement detection module 38 which may take the form of program code stored in memory executed by the same processor as the controller.

The ultrasound scanner has a one-dimensional (curved or straight line) array of ultrasound transducers 24 and a transmit beamformer 22 (comprising the transmit circuitry) which generates electrical signals in use to drive the ultrasound transducers to generate ultrasound pulses focussed in turn on specific scan positions 6 along scan lines 8 within a scan region 10. Typically pulses are focussed along individual scan lines and thereby pass the scan positions within that line in turn. The scan lines and scan positions are defined relative to the position of the array of ultrasound transducers by the timing and phase of the ultrasound pulses which are generated, and by the configuration of receive beamformer 26 (functioning as the beam processor and comprising the receive circuitry) which is configured to extract ultrasound pulse echoes from measurements made by the ultrasound transducers.

The scanner also comprises a beamformed data processor 28 configured to carry out standard data processing steps on raw ultrasound data such as band-pass filtering, detection and log compression and to output ultrasound measurement data 29. An optional compressor module 30 is configured to receive and compress ultrasound measurement data output by the beamformed data processor and there is a Wi-Fi transceiver 32 (functioning as the wireless transmitter), having a transmit buffer 34, for transmitting (optionally compressed) ultrasound measurement data from the compressor module in use.

The scanner has one or more internal (replaceable or integral) batteries 35 (optional rechargeable) which supplies all of the power to the scanner during use. The scanner may also have an interface for receiving power from an external source (e.g. a power cable) but external power sources may often be unavailable.

The ultrasound data processor 4 which is used with the ultrasound probe comprises a Wi-Fi transceiver 40 which functions as a wireless receiver and a decompression module 42 configured to decompress compressed ultrasound measurement data received from the Wi-Fi transceiver (where required). Wi-Fi is a wireless radio transmission protocol specified by the IEEE 802.11 standards. (Wi-Fi is a trade mark of the Wi-Fi Alliance).

An image processor 44 is provided to calculate ultrasound image data from the ultrasound measurement data is coupled to a display interface 46 which transmits images to the display screen 50 in use for display. The ultrasound data processor has a display screen 50. In some embodiments video generated by the ultrasound data processor is additionally or alternatively displayed on a remote display, for example on goggles worn by a user.

The ultrasound data processor may be a dedicated computing device or a smart phone or tablet running a suitable application program, such as an iPhone, iPad or other iOS device (iPhone, iPad and iOS are trade marks of Apple Inc.) or a mobile telephone or tablet executing the Android operating system (Android is a trade mark of Google Inc.).

One skilled in the art will appreciate that the extent to which the functionality of the components of the ultrasound scanner and ultrasound data processor are implemented as standalone circuits or as program code instructions executed by a processor is a matter of design choice. For example, the compressor and decompressor (where present) might be implemented by a processor executing program code or with dedicated circuits. The transmit beamformer, receive beamformer and Wi-Fi transceivers include dedicated circuitry but may be implemented in part by the processor.

In embodiments in which the ultrasound scanner comprises both a body 5 and an ultrasound probe 3 the distribution of the components shown in FIG. 1 between the body and probe is a matter of design choice. Some or all of the transmit and receive circuitry, for example, may be in the ultrasound probe along with the transducers.

With reference to FIG. 2, during operation the controller 20 regulates the transmit beamformer to generate 100 ultrasound pulses which are focused in turn on scan positions 6 spaced apart along the length of scan lines 8 in the scan region 10. Ultrasound echoes are received 102 by the ultrasound transceiver array and beamformed 104. The controller regulates the rate at which ultrasound frames are scanned, the number of scan lines in each ultrasound frame and the number of positions in each scan line where ultrasound pulses are focused and from which ultrasound echoes are received and measured. In this way, the controller determine the average rate at which ultrasound pulses are generated. One skilled in the art will be aware of standard ultrasound techniques for controlling transmit and receive beamformers to scan the scan positions.

Thus, the ultrasound scanner transmits ultrasound pulses from a number of transducers, synchronised to focus on individual scan positions, at varying depths within individual scan lines, and repeats the process to scan line across the scan region which is effectively a slice through a region of interest. The process is then repeated to rescan the region of interest. The data concerning each scan through the region of interest is an ultrasound frame. There is a standard ultrasound frame rate, number of scan lines and number of scan positions per scan line, thereby determining a standard rate of generation of ultrasound pulses, referred to herein as the main operating mode. The ultrasound frame rate, number of scan lines and number of scan positions per scan line in the main operating mode may be preprogrammed and/or depend on user instructions.

The beamformed data is pre-processed 106 by the beamformed data processor 28. This step includes data processing steps which are typically carried out on raw beamformed ultrasound measurement data such as band-pass filtering, detection and log compression. The beamformed data processor processes data concerning individual frames one at a time and within each frame processes data concerning individual scan lines one at a time.

The output from the beamformed data processor is ultrasound measurement data 29, which is broken down into ultrasound frame data portions 60, each of which relates to a successive ultrasound frame. An ultrasound frame data portion comprises a plurality of scan line data structures 62. Each scan line data structure relates to echoes received at different depths within individual scan lines. In this example, the scan line data is a measurement of echo brightness with depth (z) in a specific scan line. The scan line data structure also includes meta-data indicating to which slice the measurement data relates, for example it may specify an x and y position (relative to the transceiver array), angle, line length and number of scan points and/or distance between scan points.

The ultrasound measurement data is analysed 120 as it is generated to determine whether there is inactivity. This is discussed further below.

The ultrasound measurement data is also compressed 110 by, for each ultrasound frame, and then for each scan line, calculating the difference between consecutive measurements within the scan line data structure and then encoding these differences with a variable length coding algorithm (e.g. one based on a Huffman code). Data generated by the data compression module is passed to the Wi-Fi module for wireless transmission 110 to the image processor. The compressed data is stored in the transmit buffer of the Wi-Fi module until it is transmitted.

The compressed data is received 112 by the Wi-Fi module of the image processor. The decompression module 42 then decompresses the received ultrasound measurement data, by reversing the variable length encoding process to recreate the ultrasound measurement data. The image processing module 44 then processes the decompressed ultrasound measurement data and carries out typical ultrasound image generation procedures 116 known to the person skilled in the art, such as scan conversion, angle compounding frame smoothing, boundary/edge detection and so forth, and generate pictures, being individual image frames for consecutive display on a display 46 of the image processor. The image processor may be the microprocessor which functions as the controller (the CPU of the device) however video processing may be carried out with a dedicated graphics processing unit, for example using OpenGL with individual scan lines represented as OpenGL polygons.

The resulting images are then displayed on the display screen 50 or output through a video output interface. The images are displayed in real time, within 0.25 s of the ultrasound measurements which gave rise to the images. The user can therefore manoeuvre the ultrasound probe to view a region of interest of an animal and obtain real time visual feedback.

While the probe is being used, the ultrasound measurement data 29 which is generated is analysed by the movement detection module 38, for example when the measurement data for each ultrasound frame is complete. The ultrasound measurement data is analysed to determine if the ultrasound measurement data is consistent with the probe not being moved. The measurement data from one frame is stored and when the measurement data for the next frame is available, it is compared with the stored data. For each scan position for which there are measurements in both frames, the values of those measurements are compared. The differences are averaged and if the differences are less than a predetermined threshold (being an example of an inactivity criteria), it is determined that there is inactivity.

If inactivity continues to be detected for a predetermined period of time then the controller 20 controls the transmit circuitry to reduce the average rate of generation of ultrasound pulses, thereby reducing power consumption.

Figure 5:
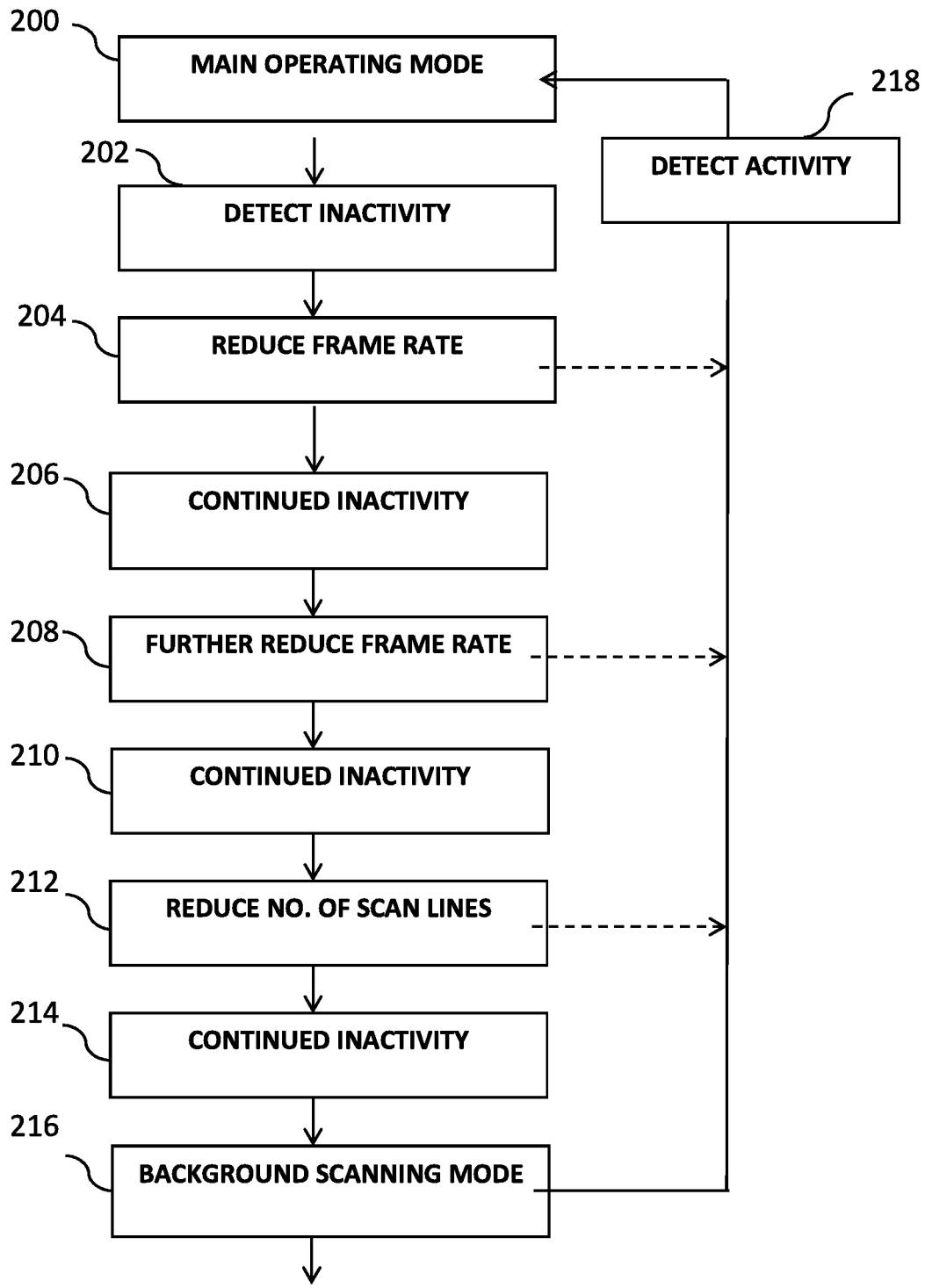
FIG. 5 is a flow chart for a procedure for reducing the average rate of generation of ultrasound pulses.

With reference to FIG. 5, the ultrasound probe is initially scanning in the main operating mode 200. Once inactivity has been detected 202 as described above for a predetermined period of time, which may be as short as 1 second, for example, the ultrasound probe moves to a first reduced power operating mode 204 in which the ultrasound frame rate is reduced. In an example, the ultrasound frame rate is halved. The number of scan lines in each ultrasound frame and the number of scan positions remain the same. Thus, the rate of generation of ultrasound pulses halves.

If inactivity continues to be detected 206 for a further period of time (e.g. a further second), the ultrasound probe moves to a second reduced power operating mode 208 in which the ultrasound frame rate is reduced again, in an example to one tenth of its original rate. The number of scan lines in each ultrasound frame and the number of scan positions remain the same. Thus, the rate of generation of ultrasound pulses is now 10% of the original rate.

If inactivity continues to be detected 210 for a further period of time (e.g. a further second), the ultrasound probe moves to a third reduced power operating mode 212 in which the ultrasound frame rate remains the same but number of scan lines is reduced. In an example, the number of scan lines is halved. Thus, the rate of generation of ultrasound pulses is now 5% of the original rate.

In some embodiments, alternate scan lines are scanned in a first ultrasound frame, and then the scan lines which were omitted in the first ultrasound frame are scanned in the following ultrasound frame. This is then repeated. This means that an image can still be generated on an ongoing basis despite the reduction in scanning. This is generally acceptable because this only takes place when there has been minimal movement for a period of time.

If inactivity continues to be detected 214 for a further period of time (e.g. a further second), the ultrasound probe moves to a third reduced power operating mode 216 in which the ultrasound frame rate and the number of scan lines are reduced still further, for example by a further factor of eight each. In this background scanning mode, ultrasound pulses are generated only with a view to detecting when the probe is moved again. In the third reduced power operating mode, the images displayed to a user stop being updated and remain the same. This can be achieved either by transmitting a message to the ultrasound image data processor to freeze the images, or simply by transmitting the same, previously measured ultrasound measurement data repetitively to the ultrasound image data processor. This is acceptable because it has been detected that the ultrasound probe is not moving. If the user is continuing to view the display it is likely that they want the image to stay the same.

In due course it will be detected 218 that the inactivity criteria is no longer met because the ultrasound probe is being moved again. When this happens, and whichever reduced power operating mode the device is in at the time, the controller switches straight to the main operating mode, possibly even during an ultrasound frame. Once a user starts to move the probe again it is likely that they want to continue to move the probe and obtain real time images straight away.

Thus, the power consumption of the transmit circuitry, and therefore the ultrasound probe, is reduced when the ultrasound probe is inactive. It does not matter that rapidly updated images are not provided to the user because it is detected that they are not moving the ultrasound probe significantly.

In an alternative low power operating mode, the ultrasound frame rate remains reasonably high, potentially as high as in the main operating mode, but the number of scan lines is reduced to minimal (e.g. one). This may be advantageous over the third reduced power operating mode described above in some circumstances as it may allow movement to be detected more quickly when it occurs.

One skilled in the art will appreciate that inactivity could be determined in various different ways, for example:

The ultrasound measurement data from one ultrasound frame may be processed to detect one or more features within the scan region (e.g. boundaries, internal cavities, or points of unusually strong or weak echoes). This might be determined from a characteristic high value of, or low value of, or change in measurement strength between adjacent scan positions in a scan line. A corresponding analysis may be carried out on ultrasound measurement data from a subsequent ultrasound frame. If the corresponding one or more features are in the same place, or very close, it is determined that there is inactivity.

The measurement of ultrasound echoes at a plurality of (e.g. all or a subset of) scan positions within the ultrasound measurement data relating to a single frame can be processed to determine some characteristic parameters, for example, calculating an average value (e.g. arithmetic mean, median, mode, geometric mean), variance, standard deviation or range. The same parameters may be calculated for a subsequent frame. If the parameters remains the same or similar to within a predetermined threshold, it is determined that there is inactivity.

It is generally sufficient only to consider a subset of scan lines to detect inactivity (and later to detect activity).

In some embodiments, the number of scan positions per scan line may also be reduced (e.g. in one or more reduced power modes). However, in embodiments where the scan positions within a scan line are differentiated between solely on the basis of the timing of received echoes, without requiring separate ultrasound pulses to be generated for each scan position in the scan lines, this will have a minimal effect on power consumption.

In an example, the ultrasound probe also comprises a temperature sensor 37, which may be a standalone temperature sensor or built into other functionality, for example, integrated into a processor, or part of a fan control circuit. If the temperature sensor measures a temperature which exceeds a threshold, the power expenditure can be reduced by switching to one of the reduced power operating modes, until the measured temperature return to below the threshold (or a lower temperature threshold).

The ultrasound scanner has a separate standby mode. The scanner enters the standby mode when it detects that there are no ultrasound echoes from the ultrasound pulses. This indicates that the probe is no longer in contact with an animal's flesh. In this case, the ultrasound scanner goes into a very much lower power mode. No ultrasound frame data is transmitted in the standby mode. In the standby mode, the scanner generates ultrasound pulses occasionally, e.g. every 200 ms, and the scanner powers up again if ultrasound echoes are detected.

In an alternative embodiment, the scan converted ultrasound image data is processed, instead of, or as well as, the ultrasound measurement data, to determine whether there has been inactivity. Again, inactivity can be determined by detecting that specific features have not moved, or not moved by more than a threshold. Inactivity can be determined by comparing consecutive images, or parts thereof. The scan converted ultrasound image data can later be processed to determine that there is activity again, or the ultrasound measurement data can be processed to determine that there is activity again (e.g. if the average rate of generation of ultrasound pulses is sufficiently low that a high quality image can no longer be formed).

The invention claimed is:

1. An ultrasound scanner comprising:
   an ultrasound probe which comprises one or more ultrasound sources and receivers,
   at least one battery,
   transmit circuitry configured to apply electrical signals to the ultrasound sources to generate ultrasound pulses and transmit them into a scan region,
   receive circuitry configured to measure ultrasound echoes received at the ultrasound receivers from the scan region,
   a beam processor configured to process the measured ultrasound echoes and output ultrasound measurement data, the ultrasound measurement data comprising measurements of ultrasound echoes from each of a series of scan positions in the scan region, and
   a controller configured to regulate the transmission of ultrasound pulses into the scan region by the ultrasound source and to process the ultrasound measurement data, or data derived therefrom, to determine an amount of movement of the ultrasound probe, and to reduce the average rate at which ultrasound pulses are generated responsive to the determined amount of movement of the ultrasound probe meeting at least one inactivity criterion.

2. An ultrasound scanner according to claim 1, wherein the amount of movement of the ultrasound probe is determined by analysing changes in the ultrasound measurement data, or data derived therefrom, between repeated measurements of the same scan positions.

3. An ultrasound scanner according to claim 2, wherein at least one inactivity criteria comprises that a measure of changes in the strength of ultrasound echoes between measurements of ultrasound echoes from one or more corresponding positions is below a threshold, optionally for at least a predetermined period of time.

4. An ultrasound scanner according to claim 3, wherein the at least one inactivity criteria comprises that the position of one or more features within the scan region determined from the ultrasound measurement data, or data derived therefrom, relative to the ultrasound probe, has moved by less than a threshold amount, optionally over at least a predetermined period of time and/or wherein the at least one inactivity criteria comprises that a measure of a change in a property of the strength of ultrasound echoes at a plurality of scan positions in the ultrasound measurement data is less than a predetermined threshold, optionally for at least a predetermined period of time.

5. An ultrasound scanner according to claim 1, wherein the average rate at which ultrasound pulses are generated is reduced by one or more of:
   reducing the number of scan lines;
   increasing the period between ultrasound frames; and/or
   periodically stopping generating ultrasound pulses for a period of time and then restarting.

6. An ultrasound scanner according to claim 1, having a main operating mode in which there is a predetermined average rate at which ultrasound pulses are generated, and that in the main operating mode, ultrasound measurement data, or data derived therefrom, relating to a first number of scan positions is processed to determine whether the at least one inactivity criterion is met but that in at least one mode with a reduced average rate of generation of ultrasound pulses, a second, lower number of scan positions is processed to determine whether the at least one inactivity criterion, or at least one activity criterion, is met.

7. An ultrasound scanner according to claim 1, wherein, the controller is configured to increase the average rate at which ultrasound pulses are generated again responsive to the determined amount of movement of the ultrasound probe meeting at least one activity criterion.

8. An ultrasound scanner according to claim 7, wherein when the average rate at which ultrasound pulses are generated is reduced, the average rate at which ultrasound pulses are generated is reduced progressively but when the average rate at which ultrasound pulses is generated is increased, it is increased more quickly.

9. Ultrasound apparatus comprising an ultrasound scanner according to claim 1 and an ultrasound data processor, the ultrasound data processor comprising:
   a wireless receiver configured to receive the ultrasound measurement data transmitted by the wireless transmitter, and
   an image processor configured to process decompressed data output by the data decompressor to form ultrasound images of the scan region, and
   a display interface configured to output the ultrasound images formed by the image processor.

10. A method of operating an ultrasound scanner, the ultrasound scanner comprising an ultrasound probe which comprises one or more ultrasound sources and receivers, the method comprising:
    the one or more ultrasound sources and receivers generating ultrasound pulses and receiving ultrasound echoes from a scan region,
    processing measurements of the received ultrasound echoes to thereby calculate ultrasound measurement data, the ultrasound measurement data comprising measurements of ultrasound echoes from each of a series of scan positions in the scan region, and processing the ultrasound measurement data, or data derived therefrom, to determine an amount of movement of the ultrasound probe, if the amount of movement of the ultrasound probe thereby detected meets at least one inactivity criterion, reducing the average rate at which ultrasound pulses are generated.

11. A method according to claim 10, wherein the amount of movement of the ultrasound probe is determined by analyzing changes in the ultrasound measurement data, or data derived therefrom, between repeated measurements of the same scan positions.

12. A method according to claim 10, further comprising transmitting the ultrasound measurement data through a wireless transmitter to a wireless receiver of an ultrasound data processor, and at the ultrasound data processor, processing the ultrasound measurement data to form ultrasound images of the portion of the subject, and outputting the ultrasound images.

13. An ultrasound scanner, the ultrasound scanner comprising:
- an ultrasound probe which comprises one or more ultrasound sources and receivers,
- at least one battery,
- at least one temperature sensor,
- transmit circuitry configured to apply electrical signals to the ultrasound sources to generate ultrasound pulses and transmit them into a scan region, and
- a controller configured to regulate the transmission of ultrasound pulses into the scan region by the ultrasound source and to reduce the average rate at which ultrasound pulses are generated responsive to the temperature measured by the at least one temperature sensor exceeding a threshold.

\* \* \* \* \*